(12) United States Patent
Wong et al.

(10) Patent No.: US 8,535,315 B2
(45) Date of Patent: Sep. 17, 2013

(54) APPARATUS AND METHOD FOR CUTTING COSTAL CARTILAGE

(75) Inventors: Brian J. F. Wong, Irvine, CA (US);
Cyrus Manuel, Irvine, CA (US); Allen Foulad, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 168 days.

(21) Appl. No.: 13/014,697

(22) Filed: Jan. 26, 2011

(65) Prior Publication Data

US 2012/0191093 A1 Jul. 26, 2012

(51) Int. Cl.
*A61B 17/00* (2006.01)

(52) U.S. Cl.
USPC .......................................................... 606/79

(58) Field of Classification Search
USPC . 606/79–89, 96, 167, 184–189; 83/454–455, 83/870, 915.5; 269/43, 45, 71, 75
See application file for complete search history.

(56) References Cited

U.S. PATENT DOCUMENTS

| 3,452,754 | A | 7/1969 | Stayer |
| 5,100,391 | A | 3/1992 | Schutte et al. |
| 5,447,516 | A | 9/1995 | Gardner |
| 5,461,953 | A * | 10/1995 | McCormick ...................... 83/36 |
| 5,951,580 | A | 9/1999 | Ashraf |
| 6,416,524 | B1 | 7/2002 | Critz et al. |
| 2008/0255623 | A1* | 10/2008 | Steiner et al. ............... 606/86 R |

FOREIGN PATENT DOCUMENTS

EP 104732 A1 * 4/1984

OTHER PUBLICATIONS

Lopez, et al., "Analysis of the Physical Properties of Costal Cartilage in a Porcine Model", Arch Facial Plastic Surgery, Jan.-Feb. 2007, p. 35-39, vol. 9(1).
Harris, et al., "Cartilage Warping: An Experimental Model", Plastic Reconstructive Surgey, Oct. 1993, p. 912-915, vol. 92(5).
Wong, et al., "The Porcine and Lagomorph Septal Cartilages: Models for Tissue Engineering and Morphologic Cartilage Research", Mar.-Apr. 2001, p. 109-116, vol. 15(2).

* cited by examiner

*Primary Examiner* — Todd Manahan
*Assistant Examiner* — Eric S. Gibson
(74) *Attorney, Agent, or Firm* — Marcus C. Dawes; Daniel L. Dawes (57) ABSTRACT

A double-bladed cutting device providing a practical method for obtaining costal cartilage specimens in both an operating room and research setting. The device reduces the skill and time required to fashion cartilage slices, while increasing the uniformity of the cut specimens. Furthermore, via an adjustable guide, slices can be obtained precisely from the central core of the rib. Although specimen lengths up to 4 cm are preferred, longer lengths can be attained without modification of the device. The cartilage specimen may be held in place within the device via means of compression or tension.

7 Claims, 8 Drawing Sheets

APPARATUS AND METHOD FOR CUTTING COSTAL CARTILAGE

STATEMENT OF GOVERNMENT SUPPORT

This invention was made with government support under grant number DR090349 awarded by Department of Defense Deployment Related Medical Research Program and grant number 1R21DE019026 awarded by the National Institute of Dental and Craniofacial Research. The government has certain rights in the invention.

BACKGROUND OF THE INVENTION

1. Field of the Invention

The invention relates to the field of medical tools, specifically to a cutting device used to obtain uniformly thick slices of cartilage from a costal (rib) cartilage sample.

2. Description of the Prior Art

Costal cartilage is becoming increasingly popular as a graft source for facial reconstruction. However, carving methods have not changed in decades, and continue to primarily rely upon detailed maneuvers with a scalpel. There are currently very few mechanical devices for shaping costal cartilage and the accuracy and precision of manual methods leave much to be desired.

Providing for a relatively abundant supply of cartilage, the costal margin is the only practical option for autogenous cartilage grafts when auricular and septal cartilage are depleted or if significant cartilage is required for extensive framework reconstruction. However, grafts harvested from peripheral regions of costal cartilage have the potential disadvantage of warping after graft placement. This undesirable effect is minimized and theoretically eliminated by obtaining balanced cross-sections from the central core of the rib. Such considerations demonstrate that the harvesting technique critically affects the shape dynamics and outcome of costal cartilage grafts, particularly in applications such as reconstructive rhinoplasty.

Techniques for carving cartilage have had modest progress over the past several decades. In the operating room, the scalpel remains the preferred instrument of choice. However, this method is hindered by imprecise and tune-consuming maneuvers. Obtaining flat grafts of uniform thickness using a scalpel requires skill and expertise, especially for thinner slices such as spreader grafts used for rhinoplasty. The ability to harvest uniform cartilage specimens is important because these specimens have a wide range of applications in nasal reconstruction.

Several cartilage cutting devices have been described or alluded to in the literature. Generally, these devices adhere to a common design of two parallel blades that are separated by a specific distance using a spacer at both ends. The piece of rib is first cut to a length that is no greater than the distance between the spacers. Then, the double-bladed device is pushed through the rib segment, producing a slice having approximately the same thickness as the spacer. Specifically, one device employs a guillotine-type apparatus fashioned from a traditional paper cutter lever utilizing two parallel blades. These blades are then swung down to section a rib segment. Other iterations include a cartilage cutting guillotine using razor blades in conjunction with securing the rib with gentle compression in a vise mechanism. Still other examples have adapted the guillotine concept by using four parallel blades in order to obtain a central slice and two peripheral slices. Although these devices offer a simple and rapid cutting approach alternative to the traditional scalpel, the accuracy of these devices is suspect at best.

What is needed is a simple device and method for cutting costal cartilage into well defined, uniformly thick user defined segments that are suitable for various delicate reconstructive surgeries.

BRIEF SUMMARY OF THE INVENTION

The current device is a cutting device that creates costal cartilage sections of a user-defined and highly uniform thickness. We describe our design effort and systematic examination of cutting mechanisms and designs, and then describe our prototype device and its performance capabilities.

A double-bladed cutting device providing a practical method for obtaining costal cartilage specimens in both an operating room and research setting is disclosed. The device reduces the skill and time required to fashion cartilage slices, while increasing the uniformity of the cut specimens. Furthermore, via an adjustable guide, slices can be obtained precisely from the central core of the rib. Although specimen lengths up to 4 cm are preferred, longer lengths can be attained without modification of the device. The cartilage specimen may be held in place within the device via means of compression or tension.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENT

Figure 1A:
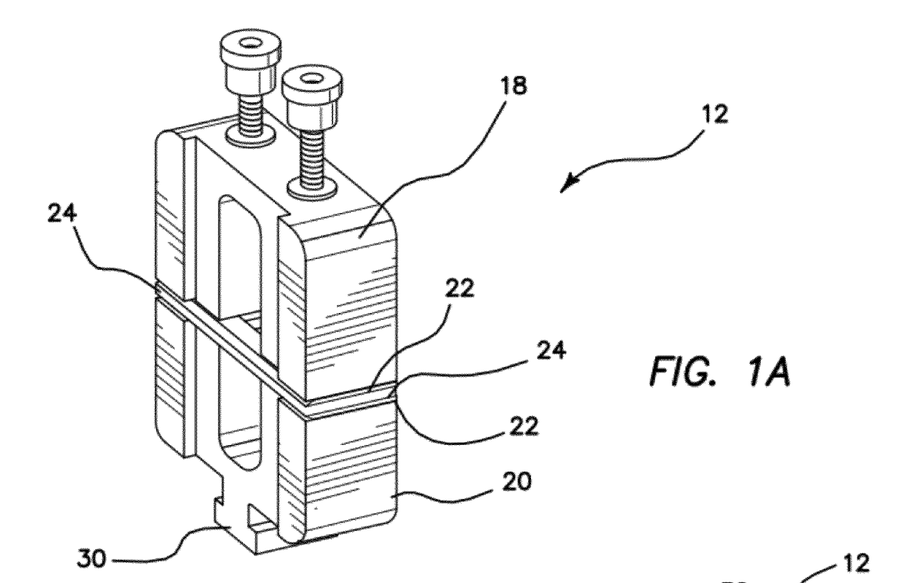
FIG. 1A is a perspective view of the cutting jig portion of the current device.
Figure 1B:
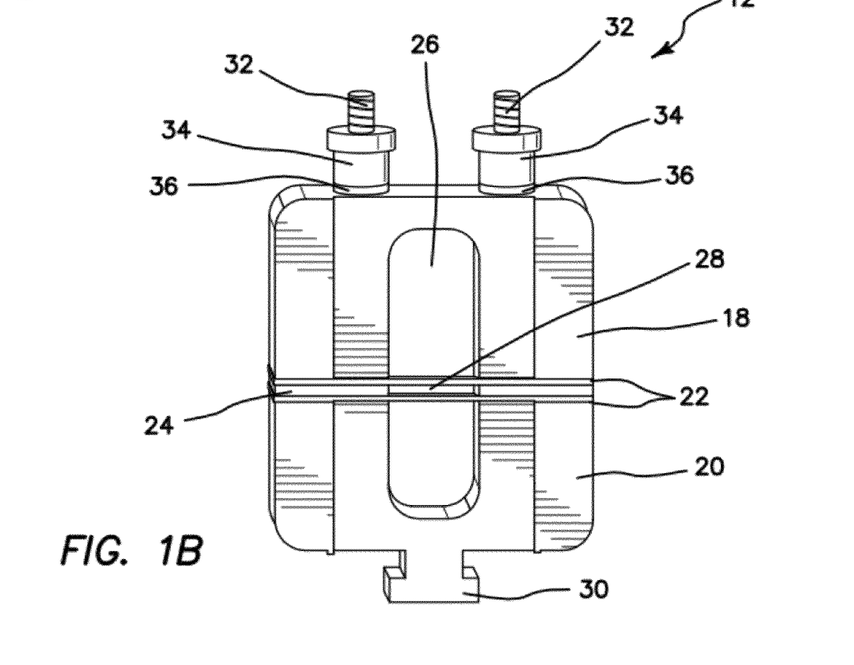
FIG. 1B is top view of the cutting jig seen in FIG. 1A.
Figure 2:
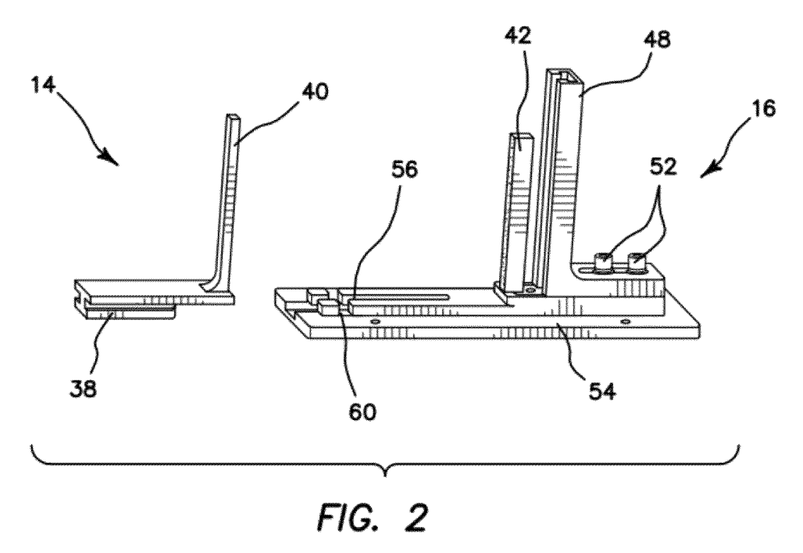
FIG. 2 is a perspective view of the specimen assembly portion of the current device, the slide member and base of the specimen assembly being separated.
Figure 3:
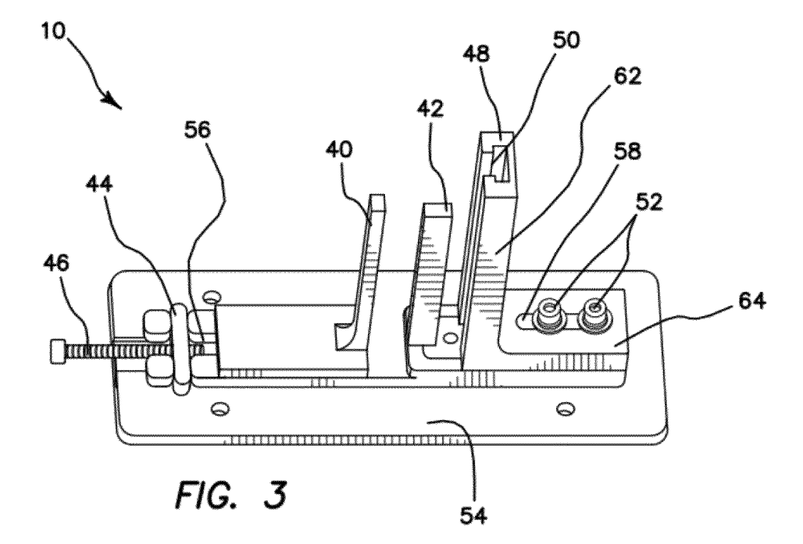
FIG. 3 is a top down perspective view of the specimen assembly, the slide member being coupled to the base.
Figure 4:
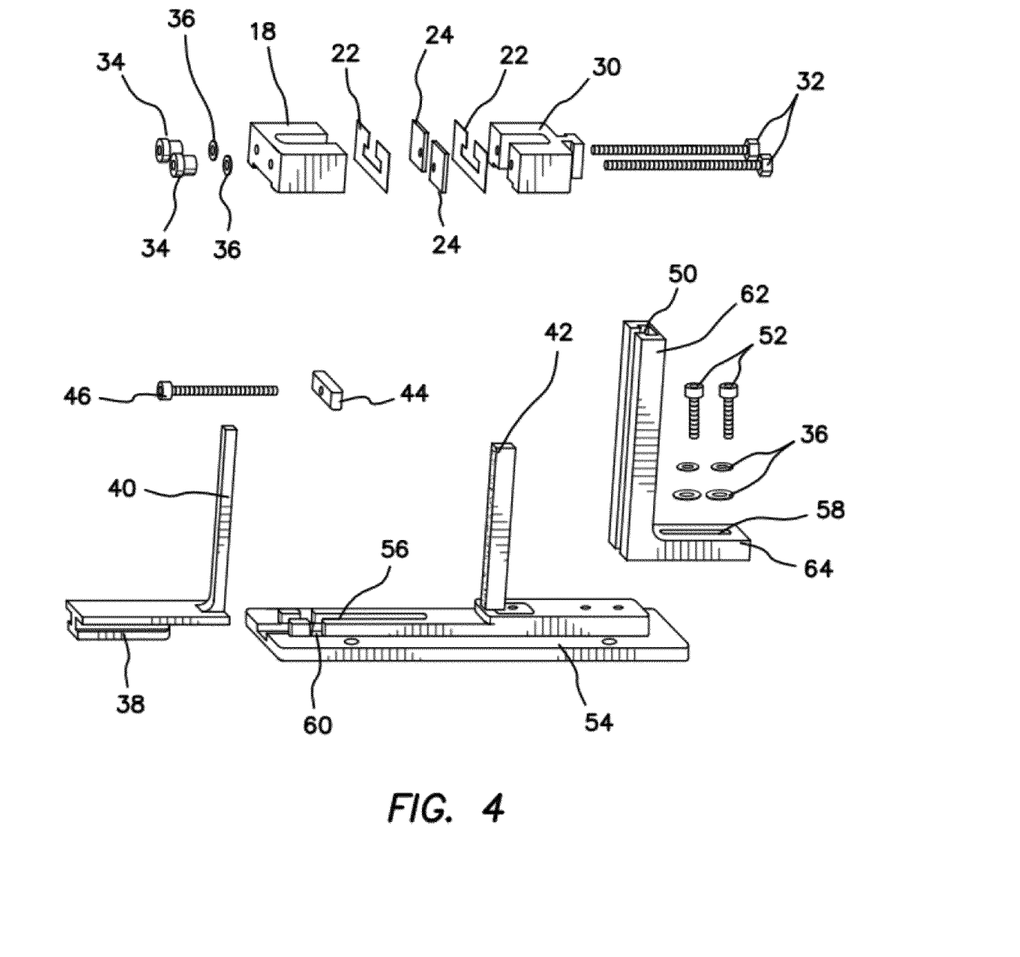
FIG. 4 is an exploded view of the cutting jig seen in FIG. 1A and the specimen assembly seen in FIG. 3.

The current device comprises three main components, a cutting jig 12 seen in FIGS. 1A and 1B, a slide member 14 and a base 16 seen in FIGS. 2 and 3. When the slide member 14 and base 16 are coupled together as seen in FIG. 3 and as further described below, a specimen assembly 10 is formed.

Turning now to the cutting jig 12 and FIGS. 1A and 1B, it can be seen that the cutting jig 12 comprises two substantially U-shaped halves, namely a top half 18 and a bottom half 20. The bottom half 20 further comprises a substantially "T" shaped jig key 30 disposed along one of its outer edges. The jig key 30 helps to guide the cutting jig 12 through the specimen assembly 10 as is further detailed below. Disposed between the top half 18 and the bottom half 20 is a pair of parallel blades 22 separated by a pair of identical aluminum spacers 24. The halves 18, 20 effectively sandwich the pair of blades 22 and spacers 24 there between and due to their substantial U-shape, define an aperture 26 in the center of the cutting jig 12. The spacers 24 maintain the blades 22 a fixed distance apart and define an aperture or cutting segment 28 which is used to cut a cartilage specimen. The cutting jig 12 is held together with the blades 22 in a locked position with the aid of a pair of jig bolts 32 inserted through both the top half 18 and bottom half 20. A corresponding pair of washers 36 and a pair of knurled nuts 34 lock the halves 18, 20 into position and prevent the blades 22 and spacers 24 from any extraneous movement.

The size and shape of the cutting segment 28 and thus the ultimate size and shape of the cut cartilage specimen may be changed or altered by the user by exchanging the spacers 24 and the blades 22 seen in FIGS. 1A and 1B for alternative blades or spacers of a differing size according to preference. For example, the cut cartilage specimen may be altered by the bevel characteristic of the blades 22. The bevel of a blade considerably affects uniformity of the resulting cut cartilage slice. Thousands of blades for commercial and industrial purposes are available from innumerable vendors and are well known in the art. In general, most blades are typically beveled on both sides of the cutting edge forming a "V" shape. This provides a thin, sharp edge for cutting. The concern of using a bi-bevel design in a double-bladed cutting device is that the distance between the beveled cutting tips of the blades is greater than the distance between the bodies of the blades themselves. Therefore, as a slice is being cut, the thickness of the slice is forced through the smaller region between the bodies of the blades and causes the blades to diverge. This leads to an even greater thickness of cartilage to be cut, and the cycle self perpetuates, leading to the creation of a wedge shaped specimen. Correspondingly, thicker blades would cause increased wedging due to a more prominent bevel and thus an even greater distance between the tips of the blades as compared to the distance between the bodies of the blades. Therefore, thinner blades will reduce this effect, but will not entirely eliminate the wedging effect. Furthermore, extremely thin blades will introduce the potential of blade flexure unless expensive stainless steel alloys or exotic aerospace industry materials are employed. The preferred embodiment is to use single beveled blades with the bevel facing outwards, which eliminates the source of wedging.

Additionally, increasing blade length results in flexure during guillotine sectioning and significantly reduces specimen thickness uniformity. To minimize blade flexure, stiffer and thicker blades can be used, but at a higher cost. To circumvent the necessity of using longer blades, the cartilage specimen can simply be cut through its long axis instead of being cut longitudinally through its short axis. This not only minimizes the blade length, but also allows any arbitrary length of cartilage to be cut using this reduced blade length.

Turn now to the slide member 14 and base 16 seen in FIG. 3. The slide member 14 comprises of a slide key 38 disposed along its bottom surface. Like the jig key 30, the slide key 38 comprises a substantially "T" shaped cross section. Disposed on the top surface of the slide member 14 is a slide post 40 which remains fixed relative to the rest of the slide member 14.

The base 16 in turn comprises a slidable or adjustable guide 48 which is anchored to a substrate 54 via a plurality of guide bolts 52. The guide 48 comprises a vertical portion 62 and a horizontal portion 64. The guide bolts 52 at first hold the guide 48 to the substrate 54 but do not tightly bind the guide 48 to it, leaving the guide 48 free to slide about a guide track 58 defined within the horizontal portion 64 as best seen in FIG. 3. The vertical portion 62 of the guide 48 comprises a substantially "T" shaped jig aperture 50 defined throughout its length. Disposed next to the guide 48 and coupled to the substrate 54 is a fixed post 42. The substrate 54 further comprises a post track 56 that is defined along its longitudinal axis. Like the jig aperture 50, the post track 56 comprises a substantially "T" shaped cross section sized and shaped to fit the slide key 38. Within the post track 56 is a gap 60 which is defined into the substrate 54 at a perpendicular orientation to that of the post track 56.

To couple the slide member 14 to the base 16 and thus form the completed specimen assembly 10 seen in FIG. 3, the slide key 38 is first inserted into the post track 56 and then slid distally. The entirety of the slide member 14 is slid past the gap 60 and a clamping bar 44 is then inserted into the gap 60 blocking any movement of the slide member 14 back in the proximal direction. A post bolt 46 is then inserted into the post track 56 and threaded through a hole defined in the clamping bar 44 thereby providing a means for the slide member 14 to be tightened against a cartilage specimen as further detailed below.

Figure 5:
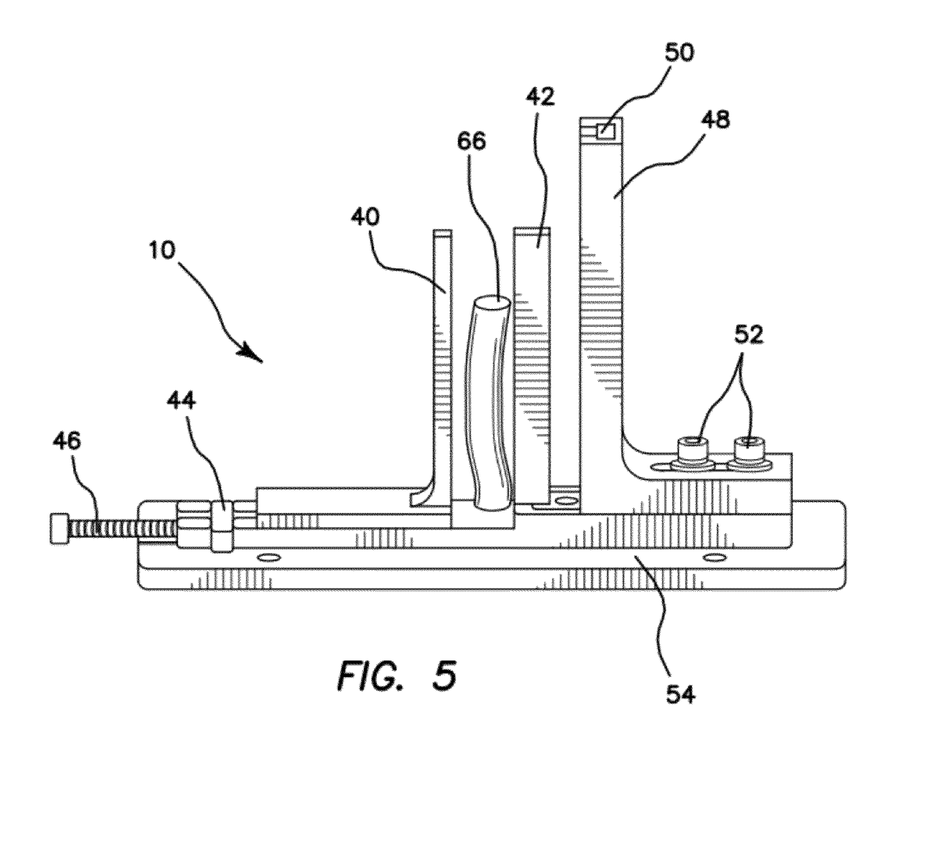
FIG. 5 is a side view of the specimen assembly with a cartilage specimen inserted between a slide post of the slide member and a fixed post of the base.

With the specimen assembly 10 fully assembled, a cartilage specimen or sample 66 is placed on the substrate 54 between the fixed post 42 and the slide post 40 in the upright position as seen in FIG. 5. While it is seen in FIG. 5 that the cartilage specimen 66 is substantially cylindrical, other shapes or sizes of cartilage may be used by one skilled in the art without departing from the original spirit and scope of the invention. Furthermore, it is to be expressly understood that materials or substances other than human costal cartilage may be cut using the current invention and that what is described herein is for illustrative purposes only.

Figure 6A:
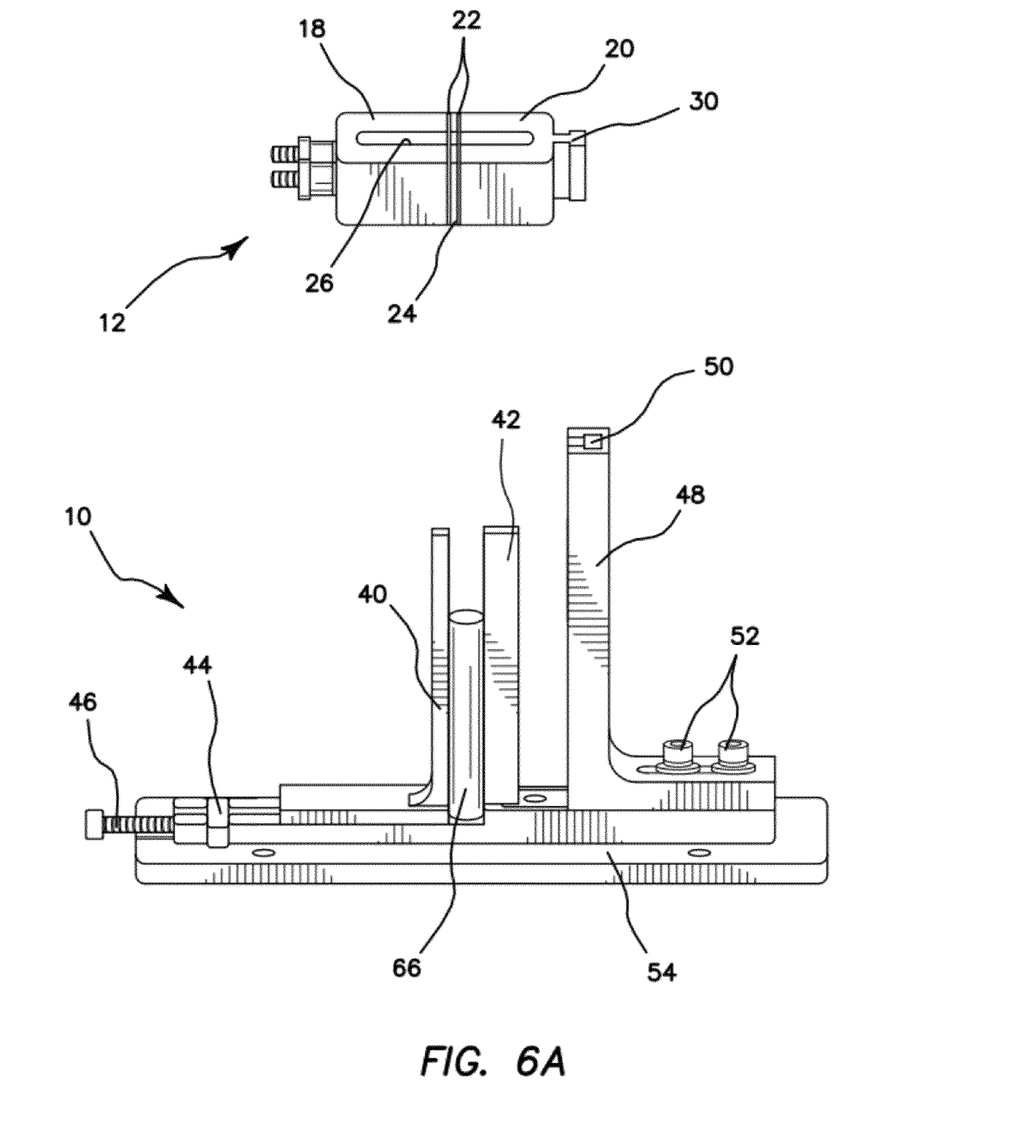
FIG. 6A is side view of the device after the slide member has been tightened to hold the specimen In a compressed grip. The cutting jig is also seen being prepared for insertion into the guide.

After sliding member 14 placement, the post bolt 46 is then rotated against the sliding member 14, pushing it distally through the post track 56. The post bolt 46 is continually manipulated until the slide post 40 is brought up against the cartilage specimen 66 and presses it against the fixed post 42, thus trapping the cartilage specimen 66 in a vice-like hold within the specimen assembly 10 as best seen in FIG. 6A. Stabilization of the cartilage specimen 66 during cutting is important to prevent specimen movement, facilitate user safety, and to provide proper positioning so that precise cuts can be made at specific regions. Ideally, the method of stabilization would also straighten curved pieces of the specimen 66, so that the blades 22 can precisely traverse the center of the specimen 66 with simple downward force. Securing the cartilage specimen 66 using a clamp is a simple option that can provide stabilization.

Figure 6B:
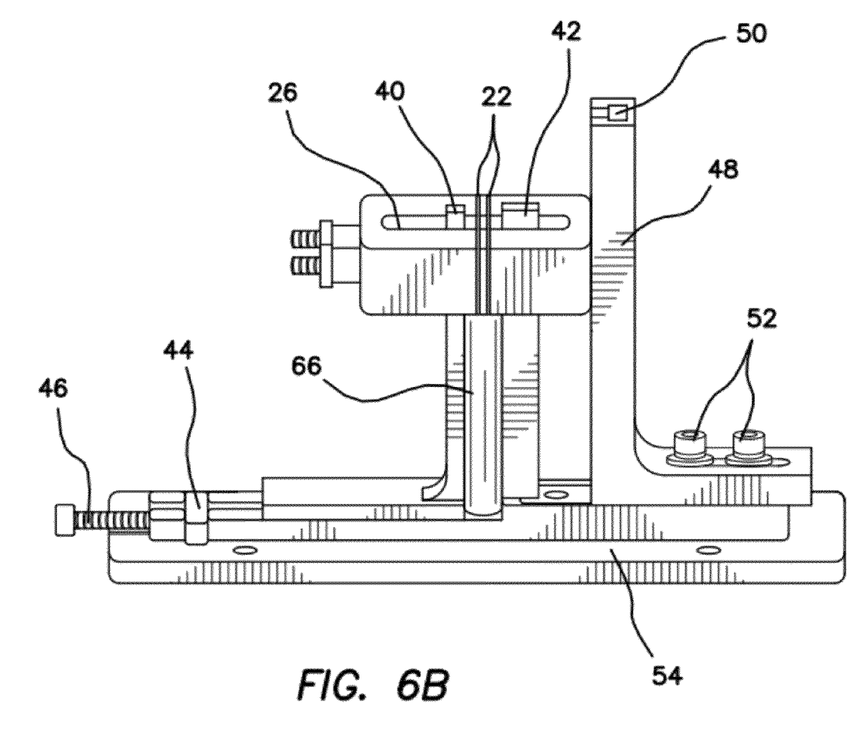
FIG. 6B is a side view of the device seen in FIG. 6A after the cutting jig has been inserted into the guide and placed just over the specimen.

The cutting jig 12 is then brought in over the top of the cartilage specimen 66 by inserting the jig key 30 into the jig aperture 50 of the guide 48. The cutting jig 12 is then slid down towards the cartilage specimen 66 until surface contact is made between the cartilage specimen 66 and the blades 22 as seen in FIG. 6B. The tops of the slide post 40 and fixed post 42 penetrate the aperture 26 defined within the cutting jig 12 so as to give the blades 22 easy and continual access to the cartilage specimen 66. The user may adjust the specific location of the blades 22 with respect to the cartilage specimen 66 by sliding the guide 48 and thus the cutting jig 12 distally and proximally through the guide track 58. When the desired cutting position has been obtained, the user fixes the guide 48 into a stationary position by tightening of the guide bolts 52 as is known in the art.

Figure 6C:
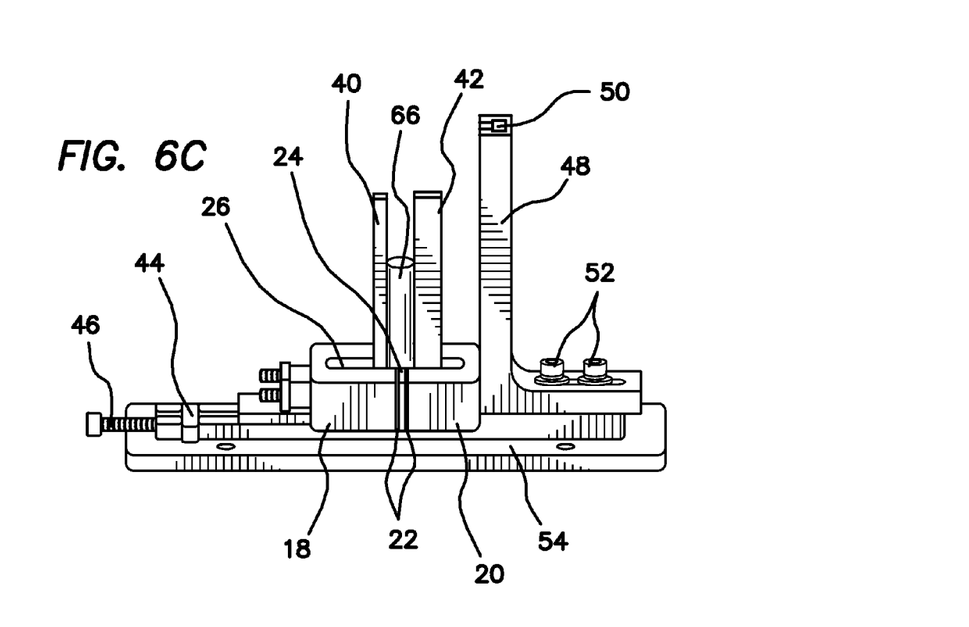
FIG. 6C is a side view of the device seen in FIG. 6B after the cutting jig has been pushed downward into the cartilage specimen, the double blades of the cutting jig creating a graft from the specimen.

With the cartilage specimen 66 and guide 48 firmly locked down into place, a downward pressure is exerted on the cutting jig 12, pressing the blades 22 into the cartilage specimen 66. The cutting jig 12 is pressed downward with the jig key 30 within the jig aperture 50 of the guide 48 until contact is made with the substrate 54 as seen hi FIG. 6C. The cutting jig 12 is then pulled upward in the opposing direction until the jig key 30 is free of the guide 48. The post bolt 46 is then loosened allowing the slide member 14 to be slid back proximally and the cartilage specimen 66 removed from the base 16.

Figure 8:
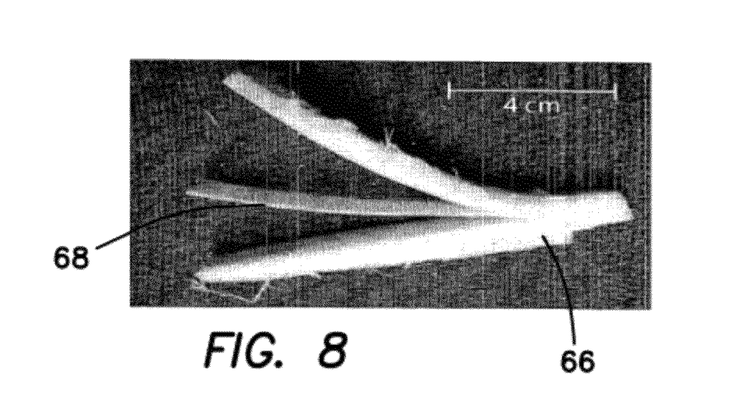
FIG. 8 is a top down view of a graft that has been cut from the cartilage specimen by the cutting jig.
Figure 9:
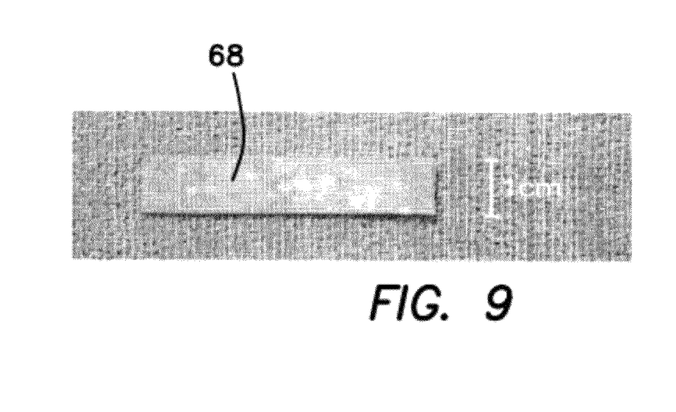
FIG. 9 is a top down view of the cartilage graft after being removed from the remainder of the cartilage specimen seen in FIG. 8.

The resultant cut made by the cutting jig 12 on the cartilage specimen 66 can be seen in FIG. 8. The double bladed design of the cutting jig 12 splits the cartilage specimen 66, producing a user-defined cartilage graft 68 suitable for a number medical procedures including but not limited to rhinoplasty. The cartilage graft 68 may be removed from the remainder of the cartilage specimen 66 as seen in FIG. 9 by a simple razor, knife, or other means known in the art.

Figure 7:
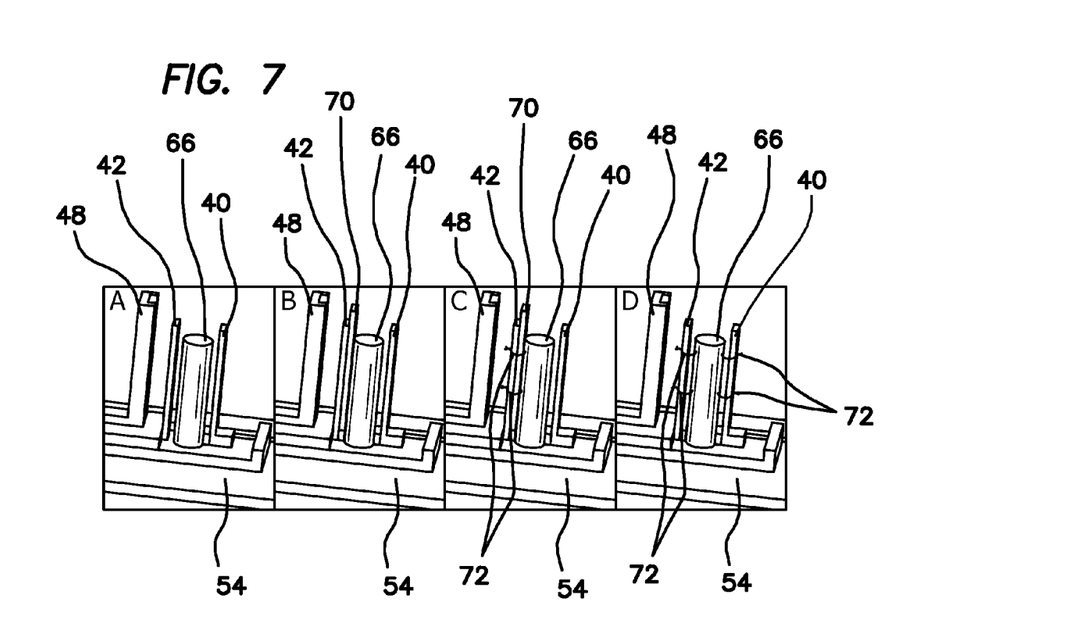
FIG. 7A is side view of an alternative embodiment of the current device in which a cartilage specimen is inserted between a slide post of the slide member and a fixed post of the base.
FIG. 7B is a side view of the alternative embodiment seen in FIG. 7A in which a vertical spacer has been inserted in between the specimen 66 and the fixed post of the base.
FIG. 7C is a side view of the alternative embodiment seen in FIG. 7B in which a plurality of sutures have been threaded through the specimen and then tied to the fixed post of the base.
FIG. 7D is a side view of the alternative embodiment seen in FIG. 7C in which the vertical spacer has been removed and an additional plurality of sutures have been threaded through the specimen and then tied to the slide post of the slide member.

An alternative means to secure the cartilage specimen 66 is through tension and can be seen in FIGS. 7A-7D. As seen in FIG. 7A, the cartilage specimen 66 is first placed between the fixed post 42 and the slide post 40 as described above. A vertical spacer 70 is then inserted between the fixed post 42 and the specimen 66 in order to provide a snug or tight fit as seen in FIG. 7B. A plurality of sutures 72 are then inserted through the specimen 66 using a common needle and thread or other means well known in the art. The free ends of the sutures 72 are then tied around the fixed post 42, thereby fixing the specimen 66 into position on at least one side as best seen in FIG. 7C. After the sutures 72 are tied to the fixed post 42, the vertical spacer 70 is removed. As seen FIG. 70, an additional plurality of sutures 72 are threaded through the opposing side of the specimen 66. The free ends of these sutures 72 are tied around the slide post 40, thereby holding the specimen 66 in a fixed vertical position. Securing the specimen 66 to the posts 40, 42 with more sutures 72 will increase the stability of the specimen 66 during cutting. This minimizes the chance of error and prevents listing of the blades 22 away from the core of the cartilage specimen 66. Therefore in critical settings, it is preferred to use at least one suture 72 per 1 cm of cartilage specimen 66 length per post 40, 42. After the cartilage specimen 66 has been properly secured to the posts 40, 42, the cutting jig 12 may then be used to cut the graft 68 in the same manner as shown and described above. After the cutting jig 12 is removed, the specimen 66 is removed from the specimen assembly 10 by severing the sutures 72.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for cutting a cartilage specimen with a user defined thickness comprising: a cutting jig; a specimen assembly comprising a base and a slide member capable of being movably coupled to the cutting jig to provide a stabilized guide for relative motion of the cutting jig with respect to the specimen assembly; wherein the stabilized guide comprises a slide post coupled to the slide member and a fixed post coupled to the base for securing the cartilage specimen to the specimen assembly, wherein the stabilized guide accommodated the cutting jig to traverse an entire length of the guide while being removably coupled thereto in order to deliver a uniform parallel and longitudinal cut to the cartilage specimen, wherein the fixed post and the slide post are configured to provide a compressive force along the cartilage specimen in order to produce flat uniform slices of cartilage, and wherein the cutting jig receives the slide post and the fixed post.

2. The apparatus of claim 1 wherein the cutting jig comprises:
   a top portion;
   a bottom portion coupled to the top portion; and
   at least two blades disposed between the top portion and the bottom portion and separated from one another by at least two spacers,
   wherein the top portion, bottom portion, and the at least two spacers define an aperture in the cutting jig, and define a cutting segment between the at least two blades and the at least two spacers, and
   wherein the at least two blades coupled within the cutting jig each comprise a cutting edge which is beveled away from a center portion or desired surface of the cartilage specimen.

3. The apparatus of claim 1 wherein the base of the specimen assembly comprises:
   a substrate;
   wherein the fixed post is fixed to the substrate;
   a post track defined into the substrate which accommodates the slide member; and
   a guide extending from the substrate, where the guide and the fixed post are adjustable relative to each other.

4. The apparatus of claim 3 wherein the cutting jig comprises a key for slidable insertion into the guide of the base and a keyway defined through the length of the guide for receiving the key and guiding relative movement of the cutting jig relative to the length of the guide.

5. The apparatus of claim 3 wherein the slide member comprises:
   the slide post;
   a key for slidable insertion into the post track defined in the substrate of the base; and
   a fastener for locking the movable post into a fixed position within the post track which allows the user to precisely select the location of the cuts along the specimen.

6. The apparatus of claim 5 wherein the fastener and the slide post are arranged and configured with respect to the post track to secure the cartilage specimen to the specimen assembly by compressing the cartilage specimen between the fixed post of the base and the slide post of the slide member.

7. The apparatus of claim 3 wherein the guide comprises:
   a coupling between the guide and the substrate to allow selective positioning of the guide on the substrate and rotation of the guide relative to the substrate; and
   a fastener for locking the guide into a fixed position and orientation on the substrate.

* * * * *